United States Patent [19]

Rudy et al.

[11] Patent Number: 4,971,782
[45] Date of Patent: * Nov. 20, 1990

[54] PERIODONTAL COMPOSITION AND METHOD

[75] Inventors: Jerome B. Rudy; Melvin Denholtz, both of Livingston; Jeffrey R. Denholtz, Stanhope, all of N.J.

[73] Assignee: Peroxydent Group, Livingston, N.J.

[*] Notice: The portion of the term of this patent subsequent to Jun. 6, 2006 has been disclaimed.

[21] Appl. No.: 721,210

[22] Filed: Apr. 9, 1985

Related U.S. Application Data

[63] Continuation-in-part of Ser. No. 532,182, Sep. 14, 1983, abandoned.

[51] Int. Cl.$^5$ .................. A61K 7/20; A61K 33/40
[52] U.S. Cl. ........................... 424/53; 424/613; 424/616
[58] Field of Search ............... 424/53, 613, 616

[56] References Cited

U.S. PATENT DOCUMENTS

| | | | |
|---|---|---|---|
| 4,487,757 | 12/1984 | Kiozpeoplou | 424/7.1 |
| 4,528,180 | 7/1985 | Schaeffer | 424/52 |
| 4,547,362 | 10/1985 | Winston et al. | 424/49 |

OTHER PUBLICATIONS

PDR–1982, (3rd ed.), pp. 561, 411, "Gly–oxide" Liquid, (Marion).

*Primary Examiner*—Shep K. Rose
*Attorney, Agent, or Firm*—Klauber & Jackson

[57] ABSTRACT

Compositions are disclosed for treating oral bacteria in the mouth, e.g., toothpaste or gel and/or tooth powders, granules, flakes or tablets. The compositions include a peroxide, a bicarbonate salt and a peroxide stabilizer.

29 Claims, No Drawings

PERIODONTAL COMPOSITION AND METHOD

This application is a continuation-in-part of U.S. application Ser. No. 532,182 filed Sept. 14, 1983, now abandoned.

The present invention relates to periodontal compositions and methods. More particularly, the invention relates to periodontal compositions including a peroxide, a bicarbonate salt and a stabilizer in, for example, a hydrophilic, non-aqueous vehicle.

Dentist and periodontists have long known that certain substances can exert powerful cleansing and sanitizing action on the teeth, the gums and the oral cavity. Hydrogen peroxide, baking soda (sodium bicarbonate) and salt (sodium chloride) are examples of such materials.

One method employing hydrogen peroxide, sodium bicarbonate and salt has been disclosed by Keyes. In the Keyes method as described in the article by Judith E. Randal in A.H. (March/April 1982), pages 82-85, and elsewhere, once a day a patient performs the following routine:

(a) Wet two tablespoons or so of baking soda with enough hydrogen peroxide to form a thick paste. (Epson salts can be substituted for baking soda for patients with high blood pressure);

(b) Use a rubber tip of the kind found on some toothbrush handles to massage the paste into the spaces between the teeth and at the gum margins on both the front and back sides of the teeth;

(c) Again using the paste, massage the gums and gum margins front and back with an electric toothbrush or a child-sized manual toothbrush;

(d) Add enough salt (or Epsom salts) to a glass of warm water so that some remains in the bottom even when the solution is stirred;

(e) Pour the liquid in part of the mixture-but not the remaining excess salt-into a Water Pik;

(f) With the device set at moderate speed, rinse the teeth and gums front and back; and (g) Run a glass of plain water through the Water Pik to prevent salt damage to its internal parts.

As is readily apparent from the above description of the Keyes method, it is a relatively complex and burdensome procedure for an individual patient to employ on a daily basis. It would be desirable for a patient to be able to perform the Keyes method or a method similarly effective in an easier manner, e.g., with a single composition.

Any attempt, however, to merely combine the components employed by Keyes into a "prepackaged" formula will not provide an effective means for accomplishing the desired results. Specifically, the hydrogen peroxide and/or sodium bicarbonate can in a combination decompose rapidly. Hydrogen peroxide (or other peroxide) can break down in the presence of alkalinity, heat, light and/or metal ions as follows:

$$2H_2O_2 \rightarrow 2H_2O + O_2(gas)$$

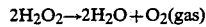

Similarly, sodium bicarbonate can break down in the presence of hydrogen peroxide, heat and/or water as follows:

$$2NaHCO_3 \rightarrow Na_2CO_3 + H_2O + CO_2(gas)$$

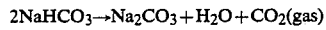

Since the active materials are lost or diminished, such a formula will have a short shelf life. Moreover, the gas evolution is especially undesirable with a tooth paste or gel, since such gas evolution can cause swelling and/or bursting of tubes containing same. All of these factors are undesirable for a consumer product.

SUMMARY OF THE INVENTION

In accordance with the present invention, it has now been found that compositions can be provided which can include a peroxide and bicarbonate in one easy to use composition and which composition is stable against peroxide and/or bicarbonate decomposition. In one aspect of the invention, a non-aqueous toothpaste or gel composition is provided comprising a peroxide, a bicarbonate salt, a peroxide stabilizer and a hydrophilic, non-aqueous vehicle which is water dispersible, water emulsifiable or water soluble, wherein the bicarbonate is present in an amount effective to provide a neutral or basic pH when the composition is contacted with water and wherein the peroxide, stabilizer and vehicle are present in amounts effective so as to inhibit decomposition of the peroxide during storage of said composition in a closed container, but so as to allow release of sufficient oxygen when the composition is contacted with water in the mouth to inhibit the motility of oral bacteria.

In another aspect of the invention, the composition is provided in tooth powder, granular, flake or tablet form and comprises a solid peroxide, a bicarbonate salt in an amount effective to provide a neutral or basic pH when the composition is contacted with water, and an effective amount of a pyrogenic colloidal silica material to inhibit decomposition of the peroxide during storage of the composition in a closed container. The pyrogenic colloidal silica material preferably comprises colloidal silica particles sintered together and having surface areas of about 50 to about 400 square meters per gram. Such pyrogenic colloidal silica has been found to provide particularly advantageous stabilizing effects.

Another composition of the invention comprises a solid peroxide and a bicarbonate salt in an amount effective to provide a neutral or basic pH when the composition is contacted with water, wherein at least one of the peroxide and the bicarbonate salt is coated with greater than about 0.5%, preferably greater than about 1.0% by weight based on the total weight of the composition of an oleophilic material to inhibit decomposition of the peroxide during storage of the composition in a closed container.

Various other aspects of the present invention, including methods of use of the compositions of the invention are discussed further below in the detailed description portion of this application.

DETAILED DESCRIPTION OF THE INVENTION

As noted above, the compositions of the invention are preferably non-aqueous. By non-aqueous, we mean that the compositions do not include water in such an amount that it will adversely affect the peroxide stability provided by the compositions of the invention, e.g., the components of the compositions of the invention consist essentially of water free materials. Preferably, the compositions of the invention include either no water or only traces of water.

The compositions of the present invention include a peroxide. Suitable peroxides include encapsulated hydrogen peroxide and any other peroxides which will allow release of nascent oxygen, e.g., upon brushing of the teeth with the composition. Thus, the peroxide can be included in the composition in compound form, e.g., as a solid organic peroxide, solid inorganic peroxide or mixtures thereof. It can also be in the form of peroxide sorbed onto an inert solid carrier so that the nascent oxygen is activated and released upon contact with saliva in the mouth or the addition of water. Further, the peroxide can be encapsulated by a water soluble, water dispersible or water emulsifiable coating (preferably edible).

Examples of suitable solid inorganic peroxides include alkali metal peroxides, alkaline earth metal peroxides, alkali metal percarbonates, alkaline earth metal percarbonates, ammonium percarbonate, zinc percarbonate, alkali metal persulfates, alkaline earth metal persulfates, ammonium persulfate, zinc persulfate, and the like and mixtures thereof with other stabilized peroxides. Suitable solid inorganic peroxides are sodium peroxide, potassium peroxide, lithium peroxide, calcium peroxide, magnesium peroxide, barium peroxide, strontium peroxide, sodium percarbonate, potassium percarbonate, calcium percarbonate, magnesium percarbonate, barium percarbonate, zinc percarbonate, sodium persulfate, potassium persulfate, calcium persulfate, magnesium persulfate, barium persulfate and zinc persulfate. A preferred solid inorganic peroxide is calcium and/or magnesium peroxide. The solid inorganic peroxide is preferably one which is soluble in an aqueous media so as to provide a suitably high concentration of oxidizing agent at the site of the periodontal disease to be treated. As noted below, these peroxides can be coated with an oleophilic material.

Examples of suitable organic peroxides include urea peroxide (percarbamide), glyceryl peroxide, benzoyl peroxide and the like. A preferred organic peroxide is urea peroxide. As noted above, the organic peroxides can be present in the composition in an encapsulated form, e.g., coated with an edible coating such as mineral oil or other oleophilic material as discussed further below.

The peroxide component of the compositions of the invention is included in an amount sufficient to allow release of sufficient oxygen when the composition is contacted with water, e.g., during brushing of teeth, to inhibit the motility of oral bacteria, e.g., in the treatment of gingivitis. Typically, the peroxide can be employed in the composition of the present invention in amounts so that at least about 1% of the composition comprises a peroxide. Preferably, the peroxide comprises from about 1 to about 20% by weight of the composition. More preferably, the peroxide comprises from about 2 to about 5% by weight of the composition. A typical peroxide concentration in the composition is about 3% by weight. The active peroxide content (i.e., the equivalent of $H_2O_2$ in the peroxide employed) is preferably between about 0.5 and about 5% by weight, more preferably between about 1 and about 3% by weight.

The bicarbonate salts employed in the composition of the invention include any which are sufficiently soluble so that, when the composition is contacted with water, e.g., in the brushing of teeth, a neutral or basic pH is provided by the bicarbonate. Suitable bicarbonates include alkali metal and alkaline earth metal bicarbonates. Examples of suitable bicarbonates include sodium bicarbonate, potassium bicarbonate, lithium bicarbonate, calcium bicarbonate, magnesium bicarbonate, and the like or mixtures thereof. A preferred bicarbonate is sodium bicarbonate. If it is desirable, e.g., with a patient having high blood pressure, etc., sodium-free compositions or low sodium compositions can be employed, such as potassium bicarbonate or magnesium bicarbonate. Combinations of bicarbonate salts can also be employed.

The bicarbonate is included in the composition of the invention in an amount sufficient to provide a neutral and basic pH when a composition is contacted with water, preferably a pH of from about 7 to about 9.5. The amount of bicarbonate actually employed in the method of the invention can vary greatly depending upon the form of the composition and its intended method of application. The bicarbonate can comprise from about 1 to about 99% by weight of the composition (e.g., in a tooth powder, granule, flake or tablet, but preferably comprises from about 1 to about 20% by weight of the composition in a tooth paste or gel, more preferably from about 2 to about 10% by weight.

The bicarbonate component can also be coated or encapsulated with an oleophilic material as discussed below, if desired. In some instances, the peroxide will not have to be encapsulated or stabilized if the bicarbonate and/or salts or other components are coated or encapsulated. For that matter, all the components could be coated or encapsulated to further ensure maximum physical and chemical stability.

It has been found in the present invention that by increasing the particle size of the bicarbonate salt, which decreases its surface area, the stability of the peroxide in the compositions of the invention is increased. For example, as among grade numbers 1, 2 and 5 baking soda available from Allied Chemical (Bulletin No. 513-016 U.S.A.), the No. 5 grade provides the greatest peroxide stability (99.1%) in the composition of the invention, (98.3%) while the No. 2 grade provides almost the same stability. Preferably, the particle size of the bicarbonate salt is such that it provides a residual peroxide level of from about 95 to about 99%, more preferably, from about 97.5 to about 99%, when the composition is stored in a closed container at room temperature for about 6 weeks. Typical screen analysis of such grades of baking soda are set forth below:

| Screen Analysis | GRADE BAKING SODA | | |
|---|---|---|---|
| | No. 1 | No. 2 | No. 5 |
| Cumulative % on | | | |
| U.S. No. 60 | | | 1 |
| 80 | | trace | 37 |
| 100 | <1 | <1 | 72 |
| 170 | 25 | 68 | 98 |
| 200 | 38 | 89 | 100 |
| 325 | 71 | 99 | |
| Bulk Density (lb/ft$^3$) | 53 | 55 | 46 |

Preferably, the bicarbonate employed in the composition of the present invention has an average particle size of from about 100 to about 2,000 microns, more preferably from about 200 to about 800 microns.

The surface area of the bicarbonate particles in the composition of the invention can be further reduced by agglomerating the particles. This can be accomplished by various means. For example, the bicarbonate salt particles can be mixed together with, for example, mineral oil or a polyethylene glycol 1000. Depending upon the amount of the mineral oil or polyethylene glycol employed, the resulting material can be in the form of agglomerated particles or in the form of a thick and extrudable paste. In the case of such a paste, the paste like material can be extruded into thin strips and then cut into small pellets containing agglomerated particles of the bicarbonate salt. Such agglomerated sodium bicarbonate salt particles preferably have an average particle size in the range of from about 100 to about 2,000 microns and can be used in the same manner as the normal bicarbonate salt in the compositions of the invention.

It should be pointed out here that relatively small amounts of chemical decomposition of the peroxide and/or bicarbonate during storage can give rise to large amounts of gases (oxygen and/or carbon dioxide) which can cause a closed container such as a tooth paste tube to swell or even explode. It has been found that in the absence of the stabilizer used in the present invention such gas evolution does, in fact, take place and can cause such swelling, etc. The present invention overcomes this problem by including suitable stabilizers which prevent breakdown of the peroxide and/or bicarbonate.

Any orally acceptable material that stabilizes the peroxide during storage of the composition in a closed container can be employed in the present composition. Examples of suitable stabilizing agents include dessicating agents, sequestering agents, colloidal particles, free radical preventatives, inorganic hardness salts, acidulating agents, coating or encapsulating materials and mixtures of such stabilizing agents.

Examples of suitable dessicating agents include magnesium sulfate, sodium sulfate, calcium sulfate, calcium chloride and colloidal silica, e.g., colloidal silica particles sintered together in chainlike formations having surface areas of from about 50 to about 400 square meters per gram such as materials sold under the trademark Cab-O-Sil by Cabot Corp. It is believed that such materials act in stabilizing the compositions of the invention by, for example, absorbing any existing water either present in or contacted with the composition so as to prevent breakdown of the peroxide and/or bicarbonate.

Examples of suitable sequestering and/or chelating agents include ethylene diamine tetraacetic acid (EDTA) or its sodium salts, nitrilotriacetic acid or its sodium salts, diethylene triamine pentaacetic acid (DTPA), or Dequest phosphonates available from Monsanto. It is believed that such chelating or sequestering agents stabilize the compositions of the invention, for example, by tying up metal ions such as $Fe^{+3}$, $Mn^{+2}$, $Cu^{+2}$, etc. that can catalyze the decomposition of peroxide in the compositions.

Other effective stabilizers for use in the present composition include colloidal particles such as the pyrogenic silica mentioned above, finely divided clays, zeolites and insoluble metallic oxides, e.g., magnesium and aluminum oxide. The pyrogenic silica materials are a preferred stabilizing agent in the compositions of the present invention.

Also, free radical inhibitors or preventatives such as butyl hydroxytoluene, butyl hydroxyanisole and beta carotene can also reduce the instability of peroxide in the composition of the invention.

Inorganic hardness salts such as calcium or magnesium inorganic compounds also reduce peroxide instability. Examples of such compounds include magnesium carbonate, magnesium chloride, calcium sulfate, calcium chloride and the like.

The addition of anhydrous acidulating agents or their salts (powdered or granulated), also provide improvement in peroxide stability in the composition of the invention. Examples of suitable acidulating agents for use in the present invention include ascorbic acid, tartaric acid, phosphoric acid as well as the chloride, sulfate or nitrate salts of calcium, magnesium or ammonium.

The inclusion of the stabilizing agent in the composition of the present invention has been found to provide significant increased stability of the compositions in comparison to compositions without such stabilizing agent. For example, when 5% by weight of pyrogenic colloidal silica (Cab-o-sil M-5) was employed in combination with 10% by weight baking soda and 10% by weight urea peroxide in a polyethylene glycol 600 vehicle (remainder), a 96% residual peroxide level was found after storage of the composition in a closed container for 18 days at room temperature. By contrast, with a similar composition omitting the pyrogenic colloidal silica, only a 90% residual peroxide level was obtained under the same conditions.

The stabilizing material is included in the composition of the invention in an amount effective so as to inhibit breakdown of the peroxide and/or sodium bicarbonate in the composition during storage in a closed container, but so as to allow release of sufficient oxygen from the peroxide when the composition is contacted with water, e.g., during brushing of teeth, to inhibit the motility of oral bacteria. Typically, the stabilizing material is included in the compositions of the present invention in an amount of from 0.1 to about 7.5%, preferably from about 1 to about 5%. For example, when pyrogenic colloidal silica materials are used as the stabilizing agent, suitable amounts thereof are from 1 to about 7.5% by weight, preferably from about 3 to about 5% by weight.

Another method for stablizing the peroxide and/or bicarbonate in the compositions of the present invention is to provide a coating on or encapsulation thereof, e.g., with an oleophilic material, which prevents the breakdown of the active materials. The presence of the coating on the peroxide and/or bicarbonate salt in the composition of the present invention also helps to prevent breakdown of the active materials by other substances, for example, by traces of water and/or by peroxide decomposition catalyzing metal ions. Preferably, the coating is an edible coating. Suitable encapsulating or coating materials include oleophilic and other materials such as conventional edible gums, polymers, resins, waxes and mineral oils. The coating is preferably rinsible from the mouth. Examples of suitable coating or encapsulating materials include Carbowax; gelatin; paraffin; xanthate gum; guar gum; materials sold under the tradename Carbopol by B. F. Goodrich; mineral oil; edible oils such as peanut oil, coconut oil, palm oil, or safflower oil; oleophilic organic esters such as isopropyl myristate or isopropyl paimitate; edible polysioxanes such as the substances sold under the trademark SS-1199 by General Electric or the commercial equivalents thereof; and the like, with mineral oil being a preferred coating material. The polysiloxanes comprise low molecular weight polysiloxanes (methyl hydrogen polysiloxane) which are polymerized and/or cross-linked by the aid of a promoter to provide a higher molecular weight polysiloxane coating on the desired active material(s). Hydrogen peroxide solution encapsulated with a mixture of paraffin and waxes is also suitable.

By employing mineral oil as olelophilic coating material for the peroxide and/or bicarbonate in the compositions of the invention, one other advantageous characteristic is provided. Specifically, oral bacteria are known to be adversely affected by oleophilic materials. Thus, the mineral oil used in the compositions of the invention will help in removing undesired bacteria during the course of treatment.

The coating should be of a thickness and composition so that it either readily dissolves, disperses or emulsifies in water, e.g., in the mouth during brushing, or disintegrates during such application to release the peroxide. For example, a coating having a thickness of from about 0.001 mm to about 0.1 mm is appropriate. Typically, the coating material can comprise from about 1 to about 3% by weight of the total composition. Preferably, the coating material comprises at least about 0.5%, more preferably at least about 1% by weight based on the total weight of peroxide and bicarbonate salt in the composition of the invention, preferably from about 1 to 5% by weight. Also, the coating materials are typically employed in a weight ratio to the material to be coated (i.e., the peroxide and/or bicarbonate salt) of from about 0.2:1 to about 5:1, preferably from about 0.5:1 to about 4:1.

When a polysiloxane is employed as the coating material for the bicarbonate salt and/or peroxide, lower amounts of this coating material can be employed. Typically, from about 0.1 to about 5% by weight based on the total weight of the composition, preferably from about 0.1 to about 1%, of the polysiloxane can be included as a coating material for the bicarbonate salt and/or peroxide in the composition.

If the material used for the coating is water insoluble, such as mineral oil, the coating phase can be pre-emulsified with a non-ionic, non-aqueous surfactant such as a hydrophilic ethoxylated sorbitan monooleate, e.g., the material sold under the trademark Tween 80. In this manner, when the composition is placed in water, the mineral oil or other olephilic coating on the particles is emulsified more readily than without the emulsification agent being present. Other similar surfactants can be employed such as sodium lauryl sulfate and other non-ionic surfactants.

Still another method of providing the desired stability in the compositions of the present invention is to provide the bicarbonate salt and peroxide in a dual phase system for a tooth paste composition. Such a dual phase system can be prepared by making a first phase containing the peroxide ingredient in a vehicle of relatively high viscosity. In a like manner, the bicarbonate salt can be mixed with a vehicle material again of relatively high viscosity to provide a second phase for the tooth paste composition of the invention. The viscosities of the respective phases can be varied to provide the desired high viscosity by employing conventional viscosity modifiers, including components of the vehicles themselves. Each phase of such a dual phase composition preferably also includes a stabilizing agent, such as pyrogenic colloidal silica, e.g., Cab-o-sil M-5. The first and second phases are placed in side-by-side contact in a closed container such as a conventional plastic tooth paste tube. The viscosities of the first and second phases are chosen so that they are sufficiently high so as to suppress diffusion between the first and second phases and thereby inhibit decomposition of the peroxide during storage of the composition in the closed container. Typically, viscosities in the range of from about 1000 cps to about 100,000 cps, preferably from about 1,000 cps to about 5,000 will provide such dual phase compositions having the desired peroxide stability.

The hydrophilic, non-aqueous vehicles employed in the tooth paste or gel composition of the present invention are water dispersible, water emulsifiable or water soluble so that they do not prevent the action of the bicarbonate and peroxide during brushing with the composition. Thus, the vehicles employed in the present invention preferably rapidly dissolve or disperse with water when used by a consumer, e.g., mouth rinse water, a pre-moistened tooth brush, saliva or post-brushing water rinse. The active species, i.e., the peroxide and bicarbonate salt may be dissolved, dispersed, emulsified or suspended in the vehicle.

Suitable hydrophilic, non-aqueous vehicles for use in the present invention include polyalkylene glycols, non-ionic surfactiants, anionic surfactants, ampholytic surfactants, cationic surfactants and alkanolamides. Also suitable are glycerol, propylene glycol or sorbitol in combination with silica, clay, polymer and/or gum thickener and perhaps dicalcium phosphate as a cleansing agent.

The hydrophilic, non-aqueous vehicles preferably provide a viscosity for the composition suitable for its use as a tooth paste or gel, e.g., between about 2,000 cps. to about 200,000 cps. If the selected vehicle does not itself provide the desired viscosity, viscosity modifiers, such as dicalcium phosphate, finely divided silica and the like may be added, and/or other vehicle agents can be included to provide such desired viscosity.

Typically, the hydrophilic, non-aqueous vehicles employed in the tooth paste or gel compositions of the invention are present in an amount of from about 45 to about 90%. Preferably, the vehicles are present in an amount of from about 85 to about 90%. molecular weight in the range of from about 400 to about 1000. Mixtures of polyethylene glycols (and for that matter other vehicles discussed herein) can be employed to provide desirable viscosity characteristics for the composition. Other suitable polyalkylene glycol vehicles include materials of the formula Suitable polyalkylene glycols for use as vehicles in the present composition include those having molecular weights of from about 200 to about 20,000. Such materials range in physical state from thin liquids to pastes to solids with increasing molecular weight. A suitable polyalkylene glycol material for use in the present invention is polyethylene glycol having a

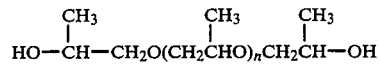

or

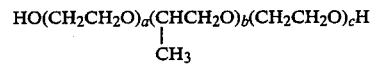

wherein n, a, b and c are integers such that the molecular weights of such materials are in the range of from about 1,100 to about 14,000. Also suitable are the polyoxyalkylene derivatives of ethylene diamine, e.g., the materials sold under the trademark Tetronic. A preferred vehicle comprises an polyethylene glycol or a mixture of polyethylene glycols of varying molecular weight to provide desirable viscosity characteristics.

Suitable non-ionic surfactants for use as the hydrophilic, non-aqueous vehicle in the tooth paste or gel composition of the invention include materials such as polyoxyethylene sorbitan fatty acid esters, e.g., materials sold under the trademark Tween. Examples of such materials are polyoxyethylene (20) sorbitan monolaurate (Tween 20), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), polyoxyethylene (5) sorbitan monooleate (Tween 81), and polyoxyethlene (20) sorbitan trioleate (Tween 85).

Polyoxyethylene fatty acid esters are also suitable for use as the vehicle in the tooth paste composition of the invention. Examples include those materials sold under the trademark Myrj such as polyoxyethylene (8) stearate (Myrj 45) and polyoxyethylene (40) stearate (Myrj 52).

Another suitable class of non-ionic surfactants for use in the vehicle in the present invention are polyoxyethylene fatty ethers, e.g., the materials sold under the trademark Brij. Examples of such materials are polyoxyethylene (4) lauryl ether (Brij 30), polyoxyethylene (23) lauryl ether (Brij 35), polyoxyethylene (2) cetyl ether (Brij 52), polyoxyethylene (10) cetyl ether (Brij 56), polyoxyethylene (20) cetyl ether (Brij 58), polyoxyethylene (2) stearyl ether (Brij 72), polyoxyethylene (10) stearyl ether (Brij 76), polyoxyethylene (20) stearyl ether (Brij 78), polyoxyethylne (2) oleyl ether (Brij 93), polyoxyethylene (10) oleyl ether, and polyoxyethylene (20) oleyl ether (Brij 99).

In one embodiment of the invention, a portion of a non-ionic surfactant employed in the vehicle in the composition of the invention can be substituted with a lipophilic surfactant, e.g., sorbitan fatty acid esters such as the materials sold under the trademark Arlacel. Suitable lipophilic surfactants include sorbitan monolaurate (Arlacel 20), sorbitan monopalmitate (Arlacel 40), sorbitan monostearate (Aracel 60), sorbitan monooleate (Arlacel 80), sorbitan sesquioleate (Arlacel 83), and sorbitan trioleate (Arlacel 85). Typically, from about 10 to about 90% of the non-ionic surfactant can be substituted by a lipophilic surfactant, preferably from about 25 to about 50%.

As noted above, other classes of surfactants such as cationic surfactants, anionic surfactants, ampholytic surfactants and alkanolamides can also be employed as the vehicle in the composition of the present invention. Such materials can be employed either by themselves as the vehicle or together with a polyakylene glycol or a non-ionic vehicle as discussed above. Examples of suitable anionic, cationic, ampholytic and alkamolamide surfactants include di-tallow dimethyl ammonium chloride, sodium lauryl sulfate, the material

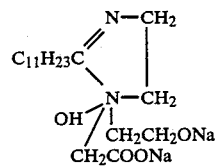

sold under the trademark Miranol, and coconut alkanolamide. Typcially, when these materials are used as part of the vehicle, they are subsituted for from about 10 to about 90% by weight, preferably from about 25 to about 50% by weight, of the main vehicle used in the composition, e.g., a polyalkalene glycol or a non-ionic surfactant as discussed above.

It has been found in the present invention that the ratio of peroxide to bicarbonate salt in the compositions of the invention has an effect on the peroxide stability in the composition. Specifically, it has been found that by decreasing the levels of bicarbonate salt and peroxide in the composition, it is possible to prepare the compositions with very good chemical and physical stability. Also, by decreasing the ratio of bicarbonate salt to the peroxide in the composition of the invention, the stability of the peroxide is also increased. Preferably, the weight ratio of peroxide to bicarbonate salt in the composition of the invention is from about 5:1 to about 0.5:1, more preferably from about 1:1 to about 4:1.

One embodiment of the invention and composition also includes chloride and/or sulfate salts such as alkali metal chlorides or sulfates, alkaline earth metal chlorides or sulfates, or mixtures thereof. Suitable chloride salts for use in the composition of the invention include sodium chloride, potassium chloride, lithium chloride, calcium chloride, magnesium chloride, sodium sulfate, potassium sulfate, magnesium sulfate, etc.

The chloride and other salts can be employed in the compositions of the invention in various amounts depending upon a number of factors, including the nature of the peroxide, and the intended use of the composition, e.g., as a mouth rinse, gel or paste, or powder. Typically, the chloride salts or other salts are included in the composition of the present invention in amounts of from about 1 to about 99% by weight of the composition. Preferably, the chloride or other salts are included in an amount of from about 1 to about 25% by weight of the composition.

The compositions of the invention can include many other components which are conventional in the art, again depending upon the ultimate use to be made of the composition. As with all the components of the composition, these components should preferably be of the class generally recognized as safe, especially for use in the mouth. For example, the composition of the invention can include a carrier for the peroxide and/or other conventional adjuvants, e.g., colorants, flavors, sanitizing agents, cleansing agents, peroxide stabilizers (e.g., acetanilide or a metal phosphate), disintegration agents for tablets (e.g., Kaolin or other clay) and the like.

In one embodiment of the invention, the composition can also be employed in a powder, granule or flake form. Any of the above mentioned adjuvants could also be included where appropriate. The powder, granule or flake material can also include conventional flow agents such as Cab-o-sil sold by the Cabot Corporation or Dry Flo sold by National Starch to prevent caking. With such a powder, granular or flake composition, the composition itself can be used, e.g., by applying a small amount of water to the material and brushing the teeth and gums therewith. Also, such powder, granule or flaked material can also be employed to be dissolved in an aqueous solution to provide, e.g., a mouthwash or rinse and/or solution for an irrigating device, e.g., a Water Pik apparatus, to be used in the treatment of the oral cavity including gums in a conventional manner.

The compositions of the present invention can be prepared by means conventional in the art. For example, the peroxide material (either encapsulated, sorbed on a solid material or a solid material itself) can be physically mixed with the bicarbonate salt and any other materials to be included in the compositions of the invention such as a chloride salt or other carriers and/or adjuvants. The composition can be prepared into a paste or gel again in a manner conventional for preparing such paste or gels as is well-known in the art by merely including the desired amount of the peroxide, stabilizer and bicarbonate in the desired hydrophilic, non-aqueous vehicle. As noted above, the paste or gel is non-aqueous.

In a preferred method of preparing a composition of the present invention, the stabilizer, such as a pyrogenic colloidal silica material, is first mixed with the hydrophlic, non-aqueous vehicle, such as polyalkylene glycol, e.g., polyethylene glycol 600 or a mixture thereof with polyethylene glycol 1000. To such mixture is added the peroxide such as urea peroxide with stirring. The peroxide can as noted above, be optionally coated with oleophilic material such as mineral oil which can also include a surfactant to pre-emulsify the coating. The bicarbonate salt is then added to the mixture containing the peroxide. The bicarbonate salt can likewise be pre-coated with an oleophilic material as discussed above. Other desired adjuvants can be added at the tail end of this process. This order of addition has been found to provide particularly good stability in comparison with methods in which the peroxide and bicarbonate are combined prior to introduction into the vehicle with the stabilizer therein.

The compositions of the present invention as noted above can be used to treat periodontal disease. In such treatment, it is believed that the composition of the invention attacks the anerobic bacteria that cause such periodontal disease. In the method of the present invention, the compositions described above are applied to the gums of the patient, e.g., a mammal such as man, in an amount effective to inhibit the bacterial motility of the oral anerobic bacteria and other bacterial types.

Thus, the compositions of the invention can be used in the form of a powder, flake or granule or for that matter as a gel or paste by applying some of such a composition to a tooth brush (perhaps pre-moistened). The teeth are then brushed in a conventional manner for about 15-60 seconds. The patient expectorates and the mouth is rinsed with water.

In another method, the compositions of the present invention can be dissolved in water for use in connection with an irrigating device, e.g., a Water Pik apparatus. In such a method, typically one quarter to one half a teaspoon of composition of the present invention would be added to the Water Pik chamber. The Water Pik treatment is performed as is conventional in the art and the mouth is then rinsed thoroughly with water.

To employ the composition of the invention as a mouthwash or rinse, one could take a small portion, e.g., a tablespoon, of the composition as a tablet, powder, etc., and add it to a small portion of water (e.g., one ounce of water) in a cup. The patient typically swishes such solution in his mouth for 15-30 seconds, expectorates and then optionally rinses the mouth with water.

It is desirable in the present invention to store the compositions of the invention in some instances with a desiccant, e.g., silica gel. For example, although urea peroxide is a relatively stable organic peroxide, it is somewhat hydroscopic and may slowly decompose. Other suitable desiccants for packaging the composition of the invention are again conventional in the art and includes magnesium sulfate and the like.

Urea peroxide is relatively stable in sealed packaging provided that it is not heated or exposed to moisture. Urea peroxide as noted above is, however, hydroscopic. In normal storage conditions, compositions containing urea peroxide do not change over several months.

The following table gives figures for urea peroxide's storage stability (in % dissociation) in tightly sealed packages under various conditions:

| Storage Time | 20° C. | 30° C. | 50° C. |
| --- | --- | --- | --- |
| 1 month | no dissociation | no dissociation | 100 |
| 2 month | no dissociation | no dissociation | |
| 3 months | 1-2 | 2-3 | |
| 12 months | 3-5 | | |

The degree of dissociation is small at low temperatures and with moisture excluded. The dissociation rises noticeably when urea peroxide is heated and above all when in moist and damp environments.

As with hydrogen peroxide itslf and its other derivatives, urea peroxide dissociates rapidly in the presence of catalysts, e.g., heavy-metal ions such as iron, copper, lead, cobalt, manganese and others. Easily oxidizable substances likewise cause dissociation. Also, certain enzymes and fermentation agents can cause urea peroxides to dissociate. Thus, such materials should be avoided in these instances.

The stabilized peroxides employed in the invention should be stable at room temperatures and in relatively dry environments (e.g., in tightly closed vessel or with a desiccant) for about 1 to about 12 months or more preferably from about 1 to about 24 months. Preferably, the compositions of the invention provide residual peroxide levels of at least about 50%, preferably at least about 70% and more preferably at least about 90%, when stored in closed containers (i.e., closed to the atmosphere and light) at room temperature for at least about 6 months or at 105° F. for 1 to 3 months.

The following examples are intended to illustrate, but not to limit, the present invention:

EXAMPLE 1

A composition in accordance with the present invention was prepared in the form of a paste or gel. A polyethylene glycol 600 is warmed and combined with a polyethylene glycol 400. This mixture is stirred and Cab-o-sil M-5 is added thereto and mixed therewith. Baking soda (Grade 5 from Church and Dwight) is mixed with mineral oil in an amount sufficient to provide 3% by weight mineral oil based on the total weight of the composition to provide a mineral oil coating on the baking soda powder. In the same manner, urea peroxide is mixed with mineral oil in an amount such that the mineral oil constitutes 0.5% by weight based on the total weight of the composition so as to provide the mineral oil coating on the urea peroxide. The coated urea peroxide is added to the polyethylene glycol/Cab-o-sil mixture and stirred. Then the coated baking soda is added with stirring. Suitable flavoring agents and sodium chloride are added to and mixed with the resulting mixture. The weight percent of the respective ingredients in the composition of the invention are listed below.

| Ingredient | % by Weight |
|---|---|
| Polyethylene glycol 400 (Sentry Grade) | 33% |
| Polyethylene glycol 600 (Sentry Grade) | 45% |
| Pyrogenic colloidal silica (Cab-o-Sil M-5) | 7.5% |
| Urea Peroxide | 3.5% |
| Baking Soda (Grade 5 from Church and Dwight) | 3.5% |
| Flavoring agents | 3.0% |
| Sodium chloride | 1.0% |
| Mineral oil | 3.5% |

This toothpaste has a commercial consistency and chemical stability (determined by permanganimetric titration) that is over 90% stable with respect to peroxide at 105° for several weeks. The conventional addition of normal flavoring agents provides the paste with a conventional tooth paste like taste.

EXAMPLE 2

A composition in accordance with the present invention was prepared by the same process as described in Example 1 above, except that the coating of the urea peroxide with the mineral oil was omitted.

EXAMPLE 3

The composition in accordance with the present invention was likewise prepared in accordance with the procedure set forth in Example 1 above, except in this instance the coatings of the bicarbonate salt and of the urea peroxide with the mineral oil were omitted. A comparison of the stability of the compositions provided by Examples 1, 2, and 3 above are set forth in Table 1 below, with the residual peroxide being determined here and throughout the examples of the application by permanganimetric titration.

TABLE 1
THE EFFECT OF OLEOPHILIC ENCAPSULATION PEROXIDE STABILITY IN TOOTH PASTE COMPOSITION

| Tooth paste System of Example No. | % Residual Peroxide (After about 1 month at) | |
|---|---|---|
| | 105° F. | 120° F. |
| 1 | 91% | 53% |
| 2 | 95% | 37% |
| 3 | 88% | 29% |

EXAMPLE 4

A toothpaste composition in accordance with the present invention was prepared by mixing together the indicated stabilizer with the vehicle component(s). The peroxide and then the bicarbonate salt are used to and mixed in with the stabilizer vehicle mixture. The resultant composition contained the ingredients listed below in the indicated proportions:

| Ingredient | % by Weight |
|---|---|
| Urea Peroxide | 10 |
| NaHCO$_3$ | varied |
| Cab-o-sil M-5 | 5 |
| Polyethylene glycol 600 (70% by wt.) } vehicle | balance to |
| Polyethylene glycol 1000 (30% by wt.) | 100% |

The NaHCO$_3$ was varied in the composition as set forth below in Table 2.

TABLE 2

| Amount NaHCO$_3$ (pbw) | % Residual Peroxide After 7 Months at Room Temperature |
|---|---|
| 5% | 63% |
| 25% | 43% |
| 33% | 24% |

These results show that lower levels of NaHCO$_3$ provide increased peroxide stability.

EXAMPLE 5

A toothpaste or gel composition in accordance with the invention was prepared in accordance with the general procedure described in Example 4 above with the ingredients listed below in the indicated proportions:

| Ingredient | % by Weight |
|---|---|
| Urea peroxide | varied |
| NaHCO$_3$ | 25 |
| Cab-o-sil M-5 | 5 |
| Polyethylene glycol 400 (30%) } vehicle | balance to |
| Polyethylene glycol 600 (38%) | 100% |
| Polyethylene glycol 1000 (32%) | |

The urea peroxide was varied in these compositions as set forth below in Table 3 and provide the indicated peroxide stabilities.

TABLE 3

| % Urea Peroxide | % Residual Peroxide After 6½ Months at Room Temperature |
|---|---|
| 2.8 | 36 |
| 5.5 | 29 |
| 8.3 | 26 |
| 10.0 | 10 |

These results demonstrate that lower levels of peroxide provide increased peroxide stability.

EXAMPLE 6

Three compositions in accordance with the present invention (Samples I, II, and III) were prepared in accordance with the general procedure described in Example 4 above with the ingredients listed below in the indicated proportions:

SAMPLE I

| Ingredient | % by Weight |
|---|---|
| Urea Peroxide | 10 |
| NaHCO$_3$ | 10 |
| Cab-o-sil M-5 | 5 |
| Polyethylene glycol 600 | 75 |

| SAMPLE II | |
|---|---|
| Ingredient | % by Weight |
| Urea Peroxide | 10 |
| NaHCO$_3$ | 20 |
| Cab-o-sil M-5 | 5 |
| Polyethylene glycol 600 | 65 |

| SAMPLE III | |
|---|---|
| Ingredient | % by Weight |
| Urea peroxide | 2.77 |
| NaHCO$_3$ | 9.14 |
| Cab-o-sil M-5 | 5 |
| Polyethylene glycol 600 | 83.1 |

The effect of the weight ratio of bicarbonate salt to peroxide in the composition of the invention is shown in Table 4 below:

TABLE 4

| Sample No. | Ratio Weight Bicarbonate to Weight Peroxide | % Residual Peroxide After 6 Months At Room Temperature |
|---|---|---|
| I | 1:1 | 60.7 |
| II | 2:1 | 22.1 |
| III | 3.3:1 | 15 |

These results demonstrate that reduced ratios of bicarbonate salt to peroxide in the compositions of the invention provide increased peroxide stability.

EXAMPLE 7

A toothpaste composition in accordance with the present invention was again prepared by the general procedure described in Example 4 above with the ingredients listed below in the indicated proportions:

| Ingredient | % by Weight |
|---|---|
| Urea Peroxide | 10 |
| NaHCO$_3$ | Varied |
| Cab-o-sil M-5 | 5 |
| Polyethylene glycol 600 | Balance to 100% |

The NaHCO$_3$ in the above formulation was varied as indicated below in Table 5 and the respective formulations provided the indicated % residual peroxide.

TABLE 5

| Weight % NaHCO$_3$ | Ratio of NaHCO$_3$ to Peroxide | % Residual Peroxide[1] |
|---|---|---|
| 10 | 1:1 | 96 |
| 15 | 1.5:1 | 97 |
| 20 | 2:1 | 91 |
| 25 | 2.5:1 | 85 |

[1]After 18 Days at Room Temperature.

These results again demonstrate that reduced NaHCO$_3$ to peroxide ratios in the compositions of the invention provides increased peroxide stability.

EXAMPLE 8

Two toothpaste compositions in accordance with the present inventions (Formulations 1 and 2) were prepared by the general procedure described in Example 4 above with the ingredients listed below in the indicated proportions:

| Ingredients | Formulation 1 % by Weight | Formulation 2 % by Weight |
|---|---|---|
| Urea Peroxide | 10 | 10 |
| NaHCO$_3$ | 10 | 10 |
| Cab-o-sil M-5 | 5 | 0 |
| Polyethylene glycol 600 | 75 | 80 |

These two formulations were tested for peroxide stability and were found to provide the results indicated below in Table 6.

TABLE 6

| Formulation No. | % Residual Peroxide After 18 Days At Room Temperature |
|---|---|
| 1 | 96% |
| 2 | 90% |

These results demonstrate the stabilizing effect even over a short time of pryogenic colloidal silica particles on the compositions of the invention.

EXAMPLE 9

A tooth paste composition in accordance with the present invention was again prepared by the general procedure described in Example 4 above with the ingredients listed below in the indicated proportions:

| Ingredients | | % by Weight |
|---|---|---|
| Urea peroxide | | 10 |
| NaHCO$_3$ | | 10 |
| Polyethylene glycol 600 (30%) | vehicle | 75 |
| Polyethylene glycol 1000 (70%) | | |
| Cab-o-sil M-5 | | 5 |

The NaHCO$_3$ material used in the above formulation was varied as to the grade employed, i.e., the particle size of the NaHCO$_3$ was varied. Grades 1, 2 and 5 NaHCO$_3$ from Church & Dwight were employed in three separate formulations Nos. 1, 2 and 3 with typical screen analysis of the various grades being as indicated below:

| Commutative % Retained On USS | Grade 1 | Grade 2 | Grade 5 |
|---|---|---|---|
| 60 | | | 3 |
| 70 | | | 10–120 |
| 100 | trace | 1 | 60–74 |
| 170 | | | 96–98 |
| 200 | 40–70 | 75–85 | |
| 325 | 70–75 | 92–96 | |

In general, the higher the grade, the coarser the particles.

The three formulations were tested for peroxide stability and the results are indicated below in Table 7.

TABLE 7

| Formulation No. | % Residual Peroxide After 42 Days At Room Temperature |
|---|---|
| 1 (Grade 1) | 95.0 |

TABLE 7-continued

| Formulation No. | % Residual Peroxide After 42 Days At Room Temperature |
|---|---|
| 2 (Grade 2) | 98.3 |
| 3 (Grade 5) | 99.1 |

These results demonstrate that coarser NaHCO3 particles with less surface areas provide compositions with better peroxide stability.

EXAMPLE 10

A toothpaste composition in accordance with the present invention can be prepared by the general procedure described in Example 4 above with the ingredients listed below in the indicated proportions:

| Ingredients | % by Weight |
|---|---|
| Urea peroxide | 4.0 |
| NaHCO3 | 4.0 |
| Cab-o-sil M-5 | 5.0 |
| Polyethylene glycol 400 (40%) } vehicle | 87.0 |
| Polyethylene glycol 600 (60%) | |

The NaCHO3 (Grade 5) can be pre-mixed with an equal amount of the mixed polyethylene glycols in a relatively dry atmosphere to prevent water absorption, e.g., in a blender. The resulting mixture is chilled and extruded. The extruded material is then chopped into small pellets and screened so as to obtain relatively coarse agglomerated baking soda particles in the size range of from about 200 to about 2000 microns. These agglomerated particles can be blended with the remaining ingredients indicated above to provide a toothpaste composition in accordance with the invention.

EXAMPLE 11

A tooth paste composition in accordance with the present invention can be prepared by the general procedure described in Example 2 above except that peanut oil can be used in place of mineral oil to provide a coated bicarbonate salt, with the overall ingredients listed below in the indicated proportions:

| Ingredients | % by Weight |
|---|---|
| Urea peroxide | 3.5 |
| NaHCO3 | 3.5 |
| Cab-o-sil M-5 | 5.0 |
| Polyethylene glycol 400 (40%) } vehicle | 85.0 |
| Polyethylene glycol 600 (60%) | |
| Peanut Oil | 3.0 |

In a similar manner, isopropyl myristate or edible silicone can be substituted for the peanut oil to provide stabilized compositions in accordance with the present invention.

EXAMPLE 12

A toothpaste composition in accordance with the present invention can be prepared by the general procedure described in Example 2 above, except that the mineral oil coating on the bicarbonate can also contain a sorbitan monooleate surfactant to co-solvate the mineral oil, with the composition having the ingredients listed below in the indicated proportions:

| Ingredients | % by Weight |
|---|---|
| Urea Peroxide | 4.0 |
| NaHCO3 | 4.0 |
| Cab-o-sil M-5 | 6.0 |
| Mineral Oil | 3.0 |
| Sorbitan Monooleate (SPAN 80) | 1.0 |
| Polyethylene glycol 400 (40%) } vehicle | 72.0 |
| Polyethylene glycol 600 (60%) | |

The mineral oil coating on the sodium bicarbonate may also include a polyoxyethylene (20) sorbitan monooleate at 0.03% by weight of the total composition in addition to the SPAN 80, thereby preemulsifying the oleophilic coating.

EXAMPLE 13

A series of toothpaste compositions in accordance with the present invention can be prepared by the general procedure described in Example 4 above employing the ingredients listed below in the indicated proportions:

| Ingredients | % by Weight |
|---|---|
| NaHCO3 | 3.5 |
| Urea Peroxide | 3.5 |
| Polyethylene glycol 400 (40%) } vehicle | 88 |
| Polyethylene glycol 600 (60%) | |
| Magnesium Sulfate Anhydrous powder | 5 |

Anhydrous sodium sulfate, calcium sulfate or calcium chloride can be substituted for the magnesium sulfate in the above formulation.

| Ingredients | % by Weight |
|---|---|
| NaHCO3 | 3.0 |
| Urea Peroxide | 3.1 |
| Polyethylene glycol 400 (40%) } vehicle | 85.9 |
| Polyethylene glycol 600 (60%) | |
| EDTA | 2.0 |
| Cab-o-sil M-5 | 4.5 |

Nitrilotriacetic acid (or its salts), diethylene triamine pentaacetic acid (or its salts), or Dequest phosphate chelating agents can be substituted for the ethylene diamine tetracetic acid (EDTA) in the above formulation.

| Ingredients | % by Weight |
|---|---|
| Urea Peroxide | 2.7 |
| NaHCO3 | 2.7 |
| Cab-o-Sil M-5 | 4.0 |
| Polyethylene glycol 400 (40%) } vehicle | 88.1 |
| Polyethylene glycol 600 (60%) | |
| Magnesium oxide | 2.5 |

Finely divided (colloidal) clays, zeolites and other insoluble metallic oxides such as aluminum oxide can be substituted for magnesium oxide in the above formulation.

| Ingredients | % by Weight | |
|---|---|---|
| Urea Peroxide | 2.0 | |
| NaHCO₃ | 2.0 | |
| Cab-o-Sil M-5 | 3.0 | |
| Polyethylene glycol 400 (40%) | vehicle | 92.0 |
| Polyethylene glycol 600 (60%) | | |
| Butyl hydroxytoluene | 1.0 | |

Butyl hydroxyanisole or beta carotene can be substituted for the butyl hydroxytoluene in the above formulation.

| Ingredients | % by Weight | |
|---|---|---|
| Urea Peroxide | 3.1 | |
| NaHCO₃ | 3.1 | |
| Cab-o-Sil M-5 | 4.5 | |
| Polyethylene glycol 400 (40%) | vehicle | 84.3 |
| Polyethylene glycol 600 (60%) | | |
| Magnesium carbonate | 5 | |

| Ingredients | % by Weight | |
|---|---|---|
| Urea Peroxide | 2.5 | |
| NaHCO₃ | 2.5 | |
| Cab-o-sil M-5 | 4.2 | |
| Anhydrous Citric Acid | 0.5 | |
| Polyethylene glycol 400 (40%) | vehicle | 91.3 |
| Polyethylene glycol 600 (60%) | | |

Ascorbic acid, tartaric acid, phosphoric acid as well as the chloride, sulfate, nitrate salts of calcium, magnesium and ammonium may be substituted for the anhydrous citric acid in the above formulation.

| Ingredients | % by Weight |
|---|---|
| Urea Peroxide | 3.75 |
| NaHCO₃ | 3.75 |
| Polyoxypropylene polyoxyethylene glycol (Pluronic L-72) | 85 |
| Cab-o-sil M-5 | 7.5 |

Pluronic-25R may be substituted for Pluronic L-72 in the above formulation.

| Ingredients | % by Weight |
|---|---|
| Urea Peroxide | 3.0 |
| NaHCO₃ | 3.0 |
| Polyoxyethylene (20) sorbitan monooleate (Tween 80) | 88.0 |
| Cab-o-sil M-5 | 6.0 |

Polyoxyethylene (2) steryl ether (Brij 72) or polyoxyethylene (8) stearate (Myri 45) may be substituted for Tween 80 in the above formulation. In addition, a portion of the Tween 80, e.g., one-half, may be substituted with polyethylene glycol 600.

| Ingredients | % by Weight |
|---|---|
| Urea Peroxide | 3.5 |
| NaHCO₃ | 3.5 |
| Polyoxyethylene (20) | 60.0 |

-continued

| Ingredients | % by Weight |
|---|---|
| sorbitan monooleate (Tween 80) | |
| Sorbitan Monooleate (Arlacel 20) | 26.0 |
| Cab-o-sil M-5 | 7.0 |

| Ingredients | % by Weight |
|---|---|
| Calcium Peroxide | 4.0 |
| NaHCO₃ | 4.0 |
| Cab-o-sil M-5 | 7.0 |
| Di-tallow dimethyl ammonium chloride | 10.0 |
| Polyethylene glycol 600 | 75.0 |

An anionic surfactant such as sodium lauryl sulfate, an ampholytic surfactant such as Miranol, or an alkanolamide such as coconut alkanolamide may be substituted for the di-tallow dimethyl ammonium chloride in the above formulation.

| Ingredients | % by Weight |
|---|---|
| Magnesium Peroxide | 5.0 |
| Potassium bicarbonate | 3.0 |
| Pluronic L-72 | 84.5 |
| Cab-o-sil M-5 | 7.5 |

The above formulation can also be prepared by replacing half of the Pluronic L-72 with polyethylene glycol 400 or polyethylene glycol 600.

The above formulations in this Example illustrate the various stabilizers and vehicles that can be used either alone or in combination in the compositions of the present invention.

EXAMPLE 14

A tooth powder in accordance with the present invention was prepared by mixing the ingredients listed below in the indicated proportions by weight:

| | Formulation No. | | | |
|---|---|---|---|---|
| Ingredients | No. 1 | No. 2 | No. 3 | No. 4 |
| Urea Peroxide | 80 | 80 | 80 | 80 |
| Cab-o-sil M-5 | 0 | 1 | 2.5 | 5.0 |
| NaHCO₃ | 10 | 9.5 | 8.75 | 7.5 |
| NaCl | 10 | 9.5 | 8.75 | 7.5 |

The above formulations were tested for peroxide stability and the results are indicated below in Table 8.

TABLE 8

| Formulation No. | % Residual Peroxide After 5 Months At Room Temperature | Physical Appearance |
|---|---|---|
| 1 | 0 | caked |
| 2 | 9.2% | slightly caked |
| 3 | 62.8% | slightly caked |
| 4 | 96.0% | free-flowing powder |

The above results show that pyrogenic colloidal silica provides significantly increased peroxide stability for the powder compositions of the present invention. In addition, this material enhances flow properties.

EXAMPLE 15

A tooth paste composition in accordance with the present invention can be made by preparing a first composition or phase containing the ingredients listed below in the indicated proportions:

| Ingredients | | % by Weight |
|---|---|---|
| Urea Peroxide | | 3 |
| Polyethylene glycol 600 (40%) | vehicle | 91 |
| Polyethylene glycol 1000 (60%) | | |
| Cab-o-sil M-5 | | 6 |

A second composition or phase can be separately prepared by mixing the ingredients listed below in the indicated proportions:

| Ingredients | | % by Weight |
|---|---|---|
| NaHCO$_3$ (Grade 5) | | 3 |
| Polyethylene glycol 600 (40%) | vehicle | 93 |
| Polyethylene glycol 1000 (60%) | | |
| Cab-o-sil M-5 | | 4 |

The first and second phases can be placed in side-by-side-relationship with a closed container such as a conventional plastic toothpaste tube. Because the first and second phases will have relatively high viscosities, they will not diffuse into one another and thereby decomposition of the peroxide during storage of the toothpaste composition in the closed container is inhibited. Upon use, the two phases will be dispersed or forced together in the mouth, e.g., by brushing to provide the desired effects on the oral bacteria.

EXAMPLE 16

The following ingredients were dry mixed to form a stable periodontal treatment composition:

| Ingredient | Amount (parts by weight-pbw) |
|---|---|
| Urea peroxide | 80 |
| Sodium bicarbonate | 10 |
| Sodium chloride | 10 |

A culture of bacteria was taken from a patient having a gum pocket typical of periodontal disease and placed on a slide. A bacterial count of this culture revealed a relatively high bacteria count with a great deal of motility.

The above composition was applied to the slide containing the bacteria culture and the slide was viewed again. It was found there was no bacterial motility after the application of the composition. This Example demonstrates the activity of the active components of the invention in treating oral bacteria.

EXAMPLE 17

In order to illustrate the efficiency of the composition of the invention, a paraffin encapsulated hydrogen peroxide solution was prepared. This encapsulated hydrogen peroxide was added to NaCl and NaHCO$_3$. The encapsulated H$_2$O$_2$ was employed in H$_2$O$_2$ concentrations of 5%, 10%, 20% and 40%, with the H$_2$O$_2$ being 35% active. These encapsulated H$_2$O$_2$ materials were mixed as follows:

| H$_2$O$_2$ Solution | NaCl and NaHCO$_3$ (1:1 by weight) |
|---|---|
| 5 pbw | 95 pbw |
| 10 pbw | 90 pbw |
| 20 pbw | 80 pbw |
| 40 pbw | 60 pbw |

A bacterial culture was employed as described in Example 1. One drop of the peroxide, NaCl and NaHCO$_3$ composition was placed on the slide. After a short time all bacterial motility ceased.

The following additional compositions can also be employed in the present invention.

EXAMPLE 18

| Ingredient | Amount (pbw-parts by weight) |
|---|---|
| Urea peroxide | 5 |
| Sodium bicarbonate | 50 |
| Sodium chloride | 45 |
| Cab-o-sil M-5 (flow agent from Cabot Corporation) | 9 (q.s.) |

EXAMPLE 19

| Ingredient | Amount (pbw) |
|---|---|
| Encapsulated hydrogen peroxide (20% solution in a paraffin-wax coating) | 5 |
| Sodium bacarbonate | 35 |
| Sodium chloride | 60 |
| Dry-flow (flow agent from National Starch) | 5 (q.s.) |

EXAMPLE 20

| Ingredient | Amount (pbw) |
|---|---|
| Urea peroxide | 15 |
| Sodium bicarbonate | 75 |
| Sodium chloride | 10 |
| Cab-o-sil-(M-5)-(Cabot Corp.) (flow agent) | 10 (q.s.) |

EXAMPLE 21

| Ingredient | Amount (pbw) |
|---|---|
| Magnesium peroxide | 2 |
| Sodium bicarbonate | 48 |
| Sodium chloride | 50 |
| Cab-O-Sil-(M-5)-(Cabot Corp.) (flow agent) | 8 (q.s.) |

EXAMPLE 22

| Ingredient | Amount (pbw) |
|---|---|
| Urea peroxide | 8 |
| Magnesium bicarbonate | 92 |

EXAMPLE 23

| Ingredient | Amount (pbw) |
| --- | --- |
| Encapsulated hydrogen peroxide (20% aqueous H₂O₂ solution in a paraffin-wax coating) | 9 |
| Lithium bicarbonate | 11 |
| Potassium chloride | 80 |

EXAMPLE 24

| Ingredient | Amount (pbw) |
| --- | --- |
| Encapsulated hydrogen peroxide (20% H₂O₂ in a paraffin-wax coating) | 15 |
| Potassium bicarbonate | 35 |
| Magnesium sulfate | 50 |

EXAMPLE 25

| Ingredient | Amount (pbw) |
| --- | --- |
| Encapsulated hydrogen peroxide (20% aqueous solution of H₂O₂ in a paraffin-wax coating)) | 12 |
| Potassium bicarbonate | 44 |
| Potassium sulfate | 44 |

EXAMPLE 26

| Ingredient | Amount (pbw) |
| --- | --- |
| Sodium percarbonate | 10 |
| Sodium bicarbonate | 20 |
| Sodium chloride | 70 |
| Cab-O-Sil-M-5 (Cabot Corp.) (flow agent) | 5 (q.s.) |

EXAMPLE 27

| Ingredient | Amount (pbw) |
| --- | --- |
| Ammonium persulfate | 10 |
| Sodium bicarbonate | 30 |
| Sodium chloride | 60 |
| Cab-O-Sil-M-5 (Cabot Corp.) (flow agent) | 6 (q.s.) |

EXAMPLE 28

| Ingredient | Amount (pbw) |
| --- | --- |
| Sodium percarbonate | 10 |
| Sodium bicarbonate | 30 |
| Sodium chloride | 60 |
| Cab-O-Sil-M-5 (Cabot Corp.) (flow agent) | 5 (q.s.) |

EXAMPLE 29

The composition of Example 18 above (10 pbw) can be mixed with a paste or gel vehicle (90 pbw) based on propylene glycol in combination silica and di-calcium phosphate. Other normal toothpaste ingredients and adjuvants could also be included in such a paste or gel.

EXAMPLE 30

The composition of Example 20 (10 pbw) can be mixed with a non-aqueous gel vehicle (90 pbw) based on xanthate gum.

EXAMPLE 31

The composition of Example 20 above (10 pbw) can be mixed with a non-aqueous gel vehicle (90 pbw) based on guar gum.

EXAMPLE 32

A non-aqueous gel comprised of propylene glycol, silica and carbopol 940 gum (B. F. Goodrich) is prepared. This gel is mixed with the composition of Example 17.

EXAMPLE 33

The composition of Example 19 above (10 pbw) can be mixed with glycerol (90 pbw) which is lyophobic to the encapsulated hydrogen peroxide. Di-calcium phosphate and/or sodium carboxy methyl cellulose can also be included in the composition.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. A non-aqueous tooth paste or gel composition comprising a peroxide selected from one or more members of the group consisting of urea peroxide, hydrogen peroxide, magnesium peroxide, calcium peroxide, lithium peroxide, sodium percarbonate, and ammonium persulfate; a bicarbonate salt; a peroxide stabilizer; and a hydrophilic, non-aqueous vehicle which is water dispersible, water emulsifiable or water soluble; wherein said bicarbonate is present in an amount effective to provide a neutral or basic pH when the composition is contacted with water; said peroxide stabilizer comprising a material selected from one or more members of the group consisting of a dessicating agent, a sequestering agent, colloidal particles, free radical preventatives, inorganic hardness salts, acidulating agents, and a coating on at least one of said peroxide and said bicarbonate salt that either readily dissolves, disperses or emulsifies in water; and wherein said peroxide, stabilizer and vehicle are present in amounts effective so as to inhibit decomposition of said peroxide during storage of said composition in a closed container, but so as to allow release of sufficient oxygen when the composition is contacted with water in the mouth to inhibit the motility of oral bacteria.

2. A composition according to claim 1, wherein said peroxide stabilizer comprises an oleophilic coating on at least one of said peroxide and said bicarbonate salt.

3. A composition according to claim 2, wherein said oleophilic coating is selected from the group consisting of a mineral oil, an edible oil, an oleophilic ester, an edible silicone compound and mixtures thereof.

4. A composition according to claim 1, wherein said peroxide stabilizer comprises an oleophilic coating comprising mineral oil on said bicarbonate salt.

5. A composition according to claim 1, wherein said peroxide stabilizer comprises a material selected from the group consisting of pyrogenic colloidal silica particles, anhydrous alkali metal or alkaline earth metal chlorides or sulfates, and mixtures thereof.

6. A composition according to claim 1, wherein the peroxide stabilizer comprises pyrogenic colloidal silica particles.

7. A composition according to claim 2, wherein sid peroxide stabilizer further comprises pyrogenic colloidal particles.

8. A composition according to claim 1, wherein said vehicle comprises polyethylene glycol having a molecular weight of between about 200 and about 2000.

9. A composition according to claim 1, wherein said bicarbonate salt is present as particles having an average size in the range of from about 100 to about 2000 microns.

10. A composition according to claim 10, wherein the peroxide is urea peroxide.

11. A composition according to claim 10, wherein the urea peroxide is coated with an oleophilic material.

12. A composition according to claim 10, wherein the bicarbonate salt is coated with an oleophilic material.

13. A composition according to claim 12, wherein the peroxide stabilizer further comprises pyrogenic colloidal silica particles.

14. A composition according to claim 13, wherein the peroxide and the bicarbonate salt are present in the composition in a weight ratio of from about 5:1 to about 0.5:1, respectively.

15. A composition according to claim 13, wherein the urea peroxide and the bicarbonate salt are present in a weight ratio of from about 5:1 to about 0.5:1, respectively.

16. A dentrifice composition comprising a peroxide selected from one or more members of the group consisting of urea peroxide, magnesium peroxide, lithium peroxide, sodium percarbonate and ammonium persulfate, a peroxide stabilizer, and bicarbonate salt particles in an amount effective to provide a neutral or basic pH when the composition is contacted with water, wherein the bicarbonate salt particles have an average particle size of about 100 microns to about 2000 microns and wherein the peroxide and peroxide stabilizer are present in amounts effective to inhibit decomposition of said peroxide during storage of the composition in a closed container, but so as to allow release of sufficient oxygen when the composition is contacted with water to inhibit the motility of oral bacteria; said peroxide stabilizer comprising a material selected from one or more members of the group consisting of a dessicating agent, a sequestering agent, colloidal particles, free radical preventives, inorganic hardness salts, acidulating agents, and a coating on at least one of said peroxide and said bicarbonate salt that either readily dissolves, disperses or emulsifies in water.

17. A composition according to claim 16, wherein said peroxide stabilizer comprises pyrogenic colloidal silica particles.

18. A dentrifice composition comprising a peroxide selected from one or more members of the group consisting of urea peroxide, hydrogen peroxide, magnesium peroxide, calcium peroxide, lithium peroxide, sodium percarbonate, and ammonium persulfate, a bicarbonate salt in an amount effective to provide a neutral or basic pH when the composition is contacted with water, and a peroxide stabilizer selected from the group consisting of a dessicating agent, a sequestering agent, colloidal particle, free radical preventatives, inorganic hardness salts, acidulating agents, and a coating on at least one of said peroxide and said bicarbonate salt that either readily dissolves, disperses or emulsifies in water and mixtures thereof, wherein said peroxide and stabilizer are present in amounts effective so as to inhibit decomposition of said peroxide during storage of said composition in a closed container, but so as to allow release of sufficient oxygen when the composition is contacted with water in the mouth to inhibit the motility of oral bacteria.

19. A process for preparing a tooth paste or gel composition, said process comprising the steps of mixing a peroxide stabilizer with a hydrophilic, non-aqueous vehicle which is water dispersible, water emulsifiable or water soluble to provide a first composition; mixing a peroxide with said first composition to provide a second composition; and mixing a bicarbonate salt with said second composition.

20. A process according to claim 19 wherein at least one of the peroxide and the bicarbonate salt is pre-coated with an oleophilic material prior to the respective mixing step.

21. A method for treating the gums of the mouth comprising a step of applying to said gums a composition in an amount effective to inhibit the bacterial motility of oral anerobic bacteria, said composition comprising a non-aqueous tooth paste or gel composition including a peroxide, selected from one or more members of the group consisting of urea peroxide hydrogen peroxide, magnesium peroxide, calcium peroxide, lithium peroxide, sodium percarbonate, and ammonium persulfate, a bicarbonate salt, a peroxide stabilizer comprising a material, selected from one or more members of the group consisting of a dessicating agent, a sequestering agent, colloidal particles, free radical preventatives, inorganic hardness salts, acidulating agents and a coating on at least one of said peroxide and said bicarbonate salt that either readily dissolves, disperses or emulsifies in water, and a hydrophilic, non-aqueous vehicle which is water dispersible, water emulsifiable or water soluble, wherein said bicarbonate is present in an amount effective to provide a neutral or basic pH when the composition is contacted with water and wherein said peroxide, stabilizer and vehicle are present in amounts effective so as to inhibit decomposition of said peroxide during storage of said composition in a closed container, but so as to allow release of sufficient oxygen when the composition is contacted with water in the mouth to inhibit the motility of oral bacteria.

22. A method for treating the gums of the mouth comprising a step of applying to said gums a composition in an amount effective to inhibit the bacterial motility of oral anerobic bacteria, said composition comprising a solid peroxide, selected from one or more members of the group consisting of urea peroxide, magnesium peroxide, calcium peroxide, lithium peroxide, sodium percarbonate, and ammonium persulfate, a bicarbonate salt in an amount effective to provide a neutral or basic pH when the composition is contacted with water, and an effective amount of a pyrogenic colloidal silica material to inhibit decomposition of the peroxide during storage of the composition in a closed container.

23. A method for treating the gums of the mouth comprising a step of applying to said gums a composition in an amount effective to inhibit the bacterial motility of oral anerobic bacteria, said composition comprising a solid peroxide selected from one or more members of the group consisting of urea peroxide, magnesium peroxide, calcium peroxide, lithium peroxide, sodium percarbonate, and ammonium persulfate, and a bicarbonate salt in an amount effective to provide a neutral or basic pH when the composition is contacted with water, wherein at least one of said peroxide and said bicarbonate salt is coated with greater than about 0.5% by weight based on the total weight of the composition of a material to inhibit decomposition of the peroxide during storage of the composition in a closed container, said coating material having a composition so that it either readily dissolves, disperses, or emulsifies in water.

24. A non-aqueous tooth paste or gel composition comprising a peroxide selected from one or more members of the group consisting of urea peroxide and hydrogen peroxide, a bicarbonate salt, a peroxide stabilizer and a hydrophilic, nonaqueous vehicle which is water dispersible, water emulsifiable or water soluble, wherein said bicarbonate is present in an amount effective to provide a neutral or basic pH when the composition is contacted with water, said peroxide stabilizer comprising a material selected from one or more members of the group consisting of a dessicating agent, a sequestering agent, colloidal particles, free radical preventatives, inorganic hardness salts, acidulating agents, and a coating on at least one of said peroxide and said bicarbonate salt that either readily dissolves, disperses or emulsifies in water, and wherein said peroxide, stabilizer and vehicle are present in amounts effective so as to inhibit decomposition of said peroxide during storage of said composition in a closed container, but so as to allow release of sufficient oxygen when the composition is contacted with water in the mouth to inhibit the motility of oral bacteria.

25. The composition of claim 24, wherein said peroxide is urea peroxide.

26. A dentrifice composition comprising a peroxide selected from one or more members of the group consisting of urea peroxide and hydrogen peroxide, a peroxide stabilizer, and bicarbonate salt particles in an amount effective to provide a neutral or basic pH when the composition is contacted with water, wherein the bicarbonate salt particles have an average particle size of about 100 microns to about 200 microns and wherein the peroxide and peroxide stabilizer are present in amounts effective to inhibit decomposition of said peroxide during storage of the composition in a closed container, but so as to allow release of sufficient oxygen when the composition is contacted with water to inhibit the motility of oral bacteria; said peroxide stabilizer comprising a material selected from one or more members of the group consisting of a dessicating agent, a sequestering agent, colloidal particles, free radical preventatives, inorganic hardness salts, acidulating agents, and a coating on at least one of said peroxide and said bicarbonate salt that either readily dissolves, disperses or emulsifies in water.

27. The composition of claim 26, wherein said peroxide is urea peroxide.

28. A method for treating the gums of the mouth comprising a step of applying to said gums a composition in an amount effective to inhibit the bacterial motility of oral anerobic bacteria, said composition comprising a non-aqueous tooth paste or gel composition including a peroxide selected from one or more members of the group consisting of urea peroxide and hydrogen peroxide; a bicarbonate salt, a peroxide stabilizer comprising a material selected from one or more members of the group consisting of a dessicating agent, a sequestering agent, colloidal particles, free radical preventatives, inorganic hardness salts, acidulating agents, and a coating on at least one of said peroxide and said bicarbonate salt that either readily dissolves, disperses or emulsifies in water; and a hydrophilic, non-aqueous vehicle which is water dispersible, water emulsifiable or water soluble; wherein said bicarbonate is present in an amount effective to provide a neutral or basic pH when the composition is contacted with water and wherein said peroxide, stabilizer and vehicle are present in amounts effective so as to inhibit decomposition of said peroxide during storage of said composition in a closed container, but so as to allow release of sufficient oxygen when the composition is contacted with water in the mouth to inhibit the motility of oral bacteria.

29. The method of claim 28, wherein said peroxide is urea peroxide.

* * * * *